United States Patent [19]
Baerveldt et al.

[11] Patent Number: 5,178,604
[45] Date of Patent: Jan. 12, 1993

[54] GLAUCOMA IMPLANT

[75] Inventors: George Baerveldt, Pasadena; Larry W. Blake, Irvine; George M. Wright, Mission Viejo, all of Calif.

[73] Assignee: Iovision, Inc., Irvine, Calif.

[21] Appl. No.: 531,010

[22] Filed: May 31, 1990

[51] Int. Cl.$^5$ ............................................. A61M 27/00
[52] U.S. Cl. ............................................ 604/8; 604/9; 604/10; 604/264; 604/294; 606/108; 623/4
[58] Field of Search .................................. 604/8-10, 604/294, 264; 623/4; 606/108

[56] References Cited

U.S. PATENT DOCUMENTS

| | | |
|---|---|---|
| 3,788,327 | 1/1990 | Donowitz et al. |
| 3,860,008 | 1/1975 | Miner et al. |
| 4,402,681 | 9/1983 | Haas et al. |
| 4,428,746 | 1/1984 | Mendez |
| 4,457,757 | 7/1984 | Molteno |
| 4,521,210 | 6/1985 | Wong |
| 4,722,724 | 2/1988 | Schocket |
| 4,729,761 | 3/1988 | White ............... 604/8 |
| 4,836,457 | 9/1989 | Lee ............... 604/294 X |
| 4,886,488 | 12/1989 | White ............... 604/9 |
| 4,902,292 | 2/1990 | Joseph ............... 604/9 |
| 4,915,684 | 4/1990 | MacKeen et al. ............... 604/8 |
| 4,936,825 | 6/1990 | Ungerlekler ............... 604/8 |
| 4,946,436 | 8/1990 | Smith ............... 604/8 |
| 4,968,296 | 11/1990 | Ritch et al. ............... 604/8 |

FOREIGN PATENT DOCUMENTS

| | | |
|---|---|---|
| 102747 | 3/1984 | European Pat. Off. |
| 168201 | 1/1986 | European Pat. Off. |
| 2160778 | 1/1986 | United Kingdom |
| 2187963 | 9/1987 | United Kingdom |

OTHER PUBLICATIONS

Alder, *Alder's Physiology of the Eye*, "Intraocular Pressure", Chapter 5, pp. 249-277.
Bickford, *Molteno Implant System*, Journal of Opthalmic Nursing & Technology, 1987, vol. 6, No. 6, pp. 224-229.
Davidovski, *Long-Term Results with the White Glaucoma Pump-Shunt*, Opthalmic Surgery, Apr., 1990, vol. 21, No. 4, pp. 288-293.
Lee, et al., *Aqueous-Venous Shunt for Glaucoma*, Surgical Techniques, Arch Opthalmol, vol. 99, Nov, 1981.
Minckler, et al., *Clinical Experience with the Single-Plate Molteno Implant in Complicated Gllaucomas*, Ophthalmology, vol. 95, No. 9, Sep., 1988, pp. 1181-1188.
Molteno, *Use of Molteno Implants to Treat Secondary Glaucoma*, Glaucoma, Grune & Stratton, Ltd., pp. 211-238.
Thomas C. White, M. D., *A New Implantable Ocular Pressure Relief Device*, University of South Dakota Medical School, Sioux Falls, S.D.
*Experience with Molteno-Type Shunts*, Ocular Surgery News, Jun. 1, 1989.
*Molteno Seton Implant*, Brochure from Staar Surgical Company.

Primary Examiner—Robert A. Hafer
Assistant Examiner—Kerry Owens
Attorney, Agent, or Firm—Kobbe, Martens, Olson & Bear

[57] ABSTRACT

An implant for use in the treatment of glaucoma is disclosed wherein the implant comprises an elastomeric plate having a non-valved elastomeric drainage tube attached thereto. The plate is elliptical in shape and curved so as to conform to the curvature of the eye. The plate is inserted into the eye in an incision made in the Tenon's capsule and sutured to the sclera. The drainage tube is tunnelled through the Tenon's capsule and cornea and inserted into the anterior chamber, thus providing patent fluid communication between the anterior chamber and the elastomeric plate. The flexible structure of the plate allows the plate to be easily inserted, thus reducing the surgical procedure length. In addition, the pliable material minimizes th risk of damage and trauma to surrounding tissues in the insertion process.

9 Claims, 5 Drawing Sheets

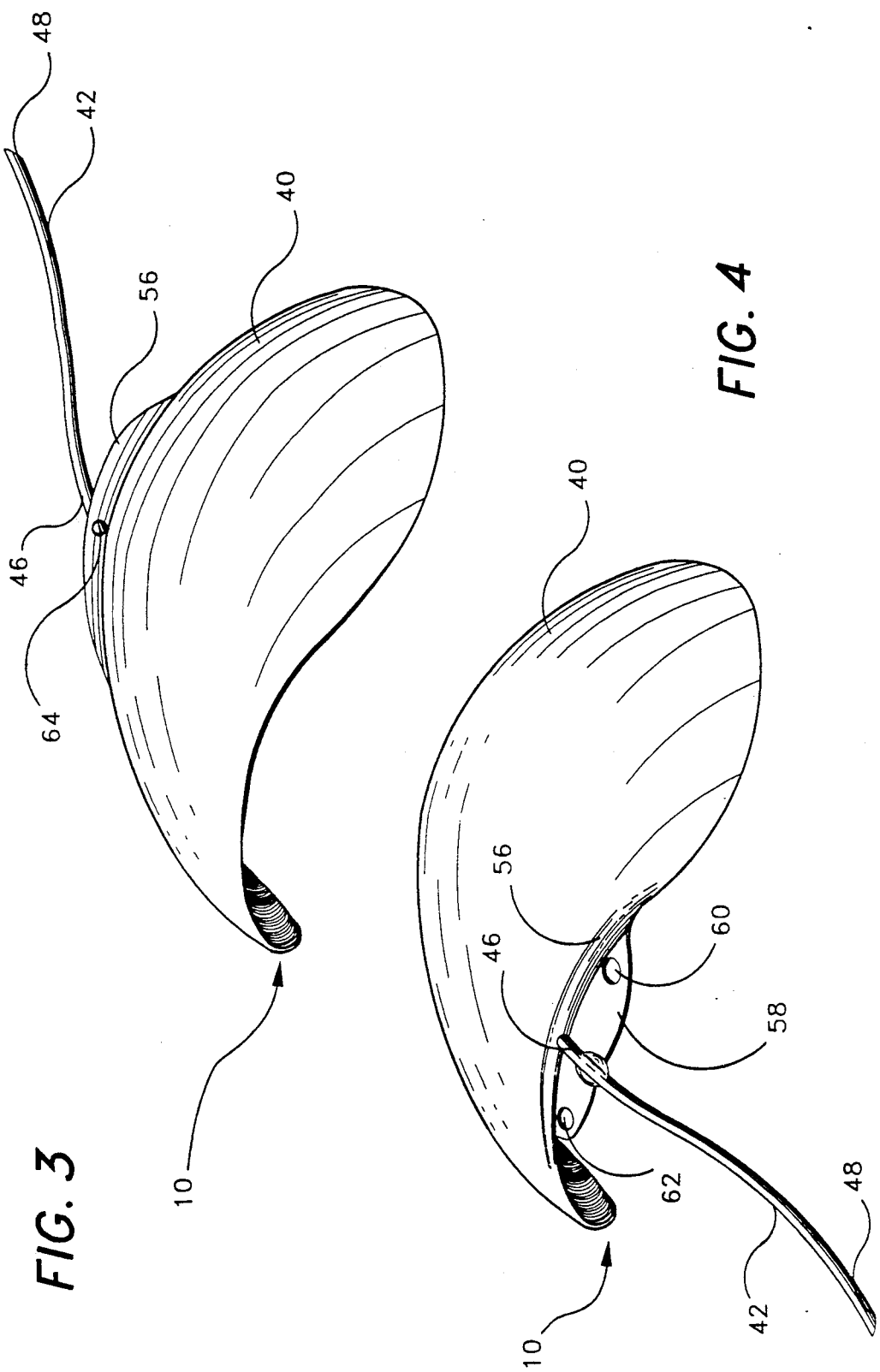

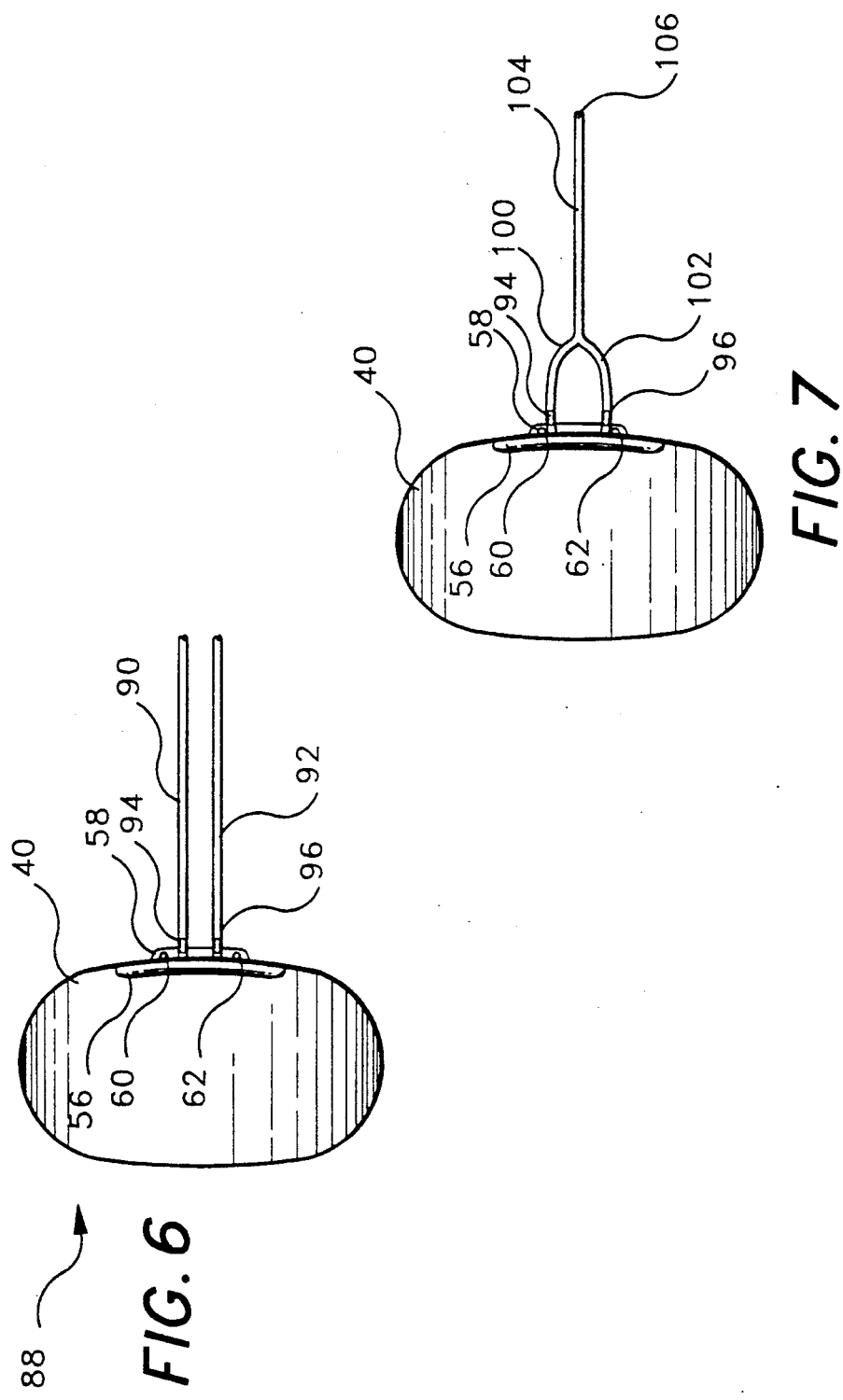

GLAUCOMA IMPLANT

FIELD OF THE INVENTION

The invention relates to ocular implants, and, in particular, to an implant used in the treatment of glaucoma.

BACKGROUND OF THE INVENTION

Aqueous is a clear, colorless fluid that fills the anterior and posterior chambers of the eye. The aqueous is formed by the ciliary body in the eye and is a carrier of nutrients for the lens. In addition, the aqueous provides a continuous stream into which surrounding tissues can discharge the waste products of metabolism.

The aqueous produced in the ciliary processes circulates from the posterior chamber to the anterior chamber of the eye through the pupil and is absorbed through the trabecular meshwork, a plurality of crisscrossing collagen cords covered by endothelium. Once through the trabecular meshwork, the aqueous passes through Schlemm's canal and into venous circulation. The rate of aqeuous outflow through the trabecular meshwork in a normal eye is typically 2.1 $\mu$L/min. Intraocular pressure in the eye is maintained by the formation and drainage of the aqueous. All the tissues within the corneoscleral coat covering the eyeball are subject to this pressure, which is higher than pressure exerted on tissues at other locations in the body.

Glaucoma is a progressive disease of the eye characterized by a gradual increase of intraocular pressure. This increase in pressure is most commonly caused by stenosis or blockage of the aqueous outflow channel, resulting in excessive buildup of aqueous fluid in the eyeball. Other causes include increase in venous pressure outside the eye which is reflected back through the aqueous drainage channels and increased production of aqueous. In a "normal" eye, intraocular pressure ranges from 4 to 12 mm mercury. In an eye with glaucoma, this pressure can rise to as much as 50 mm mercury. This increase in intraocular pressure produces gradual and permanent loss of vision in the afflicted eye.

Existing corrective methods for the treatment of glaucoma include drugs, surgery, and implants. Miotic drugs lower intraocular pressure by facilitating aqueous outflow. Beta blockers, epinephrine products, and carbonic anhydrase inhibitors which inhibit production of the aqueous, are also commonly used in pharmacological glaucoma treatment. Steroids have been used in long-term glaucoma treatment as well. However, pharmacological treatment is prohibitively expensive to a large majority of glaucoma patients. In addition, many people afflicted with the disease live in remote or undeveloped areas where the drugs are not readily accessible. The drugs used in the treatment, in particular the steroids, often have undesirable side effects and many of the long-term effects resulting from prolonged use are not yet known.

Surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye. A trabeculotomy, opening the inner wall of Schlemm's canal, is often performed in cases of open-angle glaucoma so as to increase the outflow of the aqueous, thereby decreasing intraocular pressure. While often successful, these surgical techniques possess inherent risks associated with invasive surgery on an already afflicted eye. Furthermore, the tissue of the eye can grow back to the preoperative condition, thereby necessitating the need for further treatment.

Ocular implants are often used in long-term glaucoma treatment without the disadvantages of drugs and invasive surgery. One such implant is disclosed in U.S. Pat. No. 4,457,757 entitled "Device for Draining Aqueous Humor" and commercially available as the Molteno TM Seton Implant. The implant comprises a drainage tube connected to one or more ridged plate reservoirs. The reservoir plates are designed to conform to the curvature of the eye. A reservoir plate is placed under Tenon's capsule and sutured to the sclera. The drainage tube is implanted into the anterior chamber through a scleral flap. A second plate can be implanted under the superior rectus muscle and sutured to the sclera. At this point, the body will form a tissue around these plates. Increased pressure causes the tissues above the plates to lift and form a bleb into which aqueous fluid from the anterior chamber drains via the drainage tube. Once inside the bleb, the aqeuous seeps into intercellular spaces and is removed by surrounding capillaries or lymhpatics. This type of implant is disadvantageous as the plates are formed of a rigid plastic which makes insertion beneath the eye tissue difficult and time-consuming. Furthermore, the rigid material poses a risk of irritation and/or damage to adjacent vasculature and tissue.

UK Patent Application 2,160,778 entitled "Aqueous humor drainage device" discloses a similar type of implant device comprising a drainage tube and a drainage body. The tube is fixed to and opens directly onto a surface of the body. The device is sutured to the sclera of the eye and the tube positioned within the anterior chamber so as to provide outflow for the aqueous contained therein. The device further includes a pressure gradient limiting valve formed as a slit in the tube, however, this type of valve does not allow patent, i.e., open or two-way, flow through the drainage tube. thereby preventing retrograde aqueous flow into the anterior chamber.

SUMMARY OF THE INVENTION

The present invention provides an implant for the treatment of glaucoma which can be easily inserted into an afflicted eye and which provides for patent flow between the implant and the anterior chamber of the eye. The implant comprises a single plate formed of a pliable, elastomeric material having a non-valved tube attached to and opening onto the upper surface of the plate. The pliable plate is sutured to the sclera and covered by a thick flap of Tenon's capsule so as to be encapsulated within a drainage bleb. The attached tube is tunneled out through Tenon's capsule and in through the limbus so as to provide a drain for aqueous fluid. The exposed portion of the tube is covered by a scleral graft. Because of the pliable construction and shape, the device can be implanted much quicker than previously realized with other implants. This substantially shortens the time required to perform the surgical procedure.

In a unique aspect of the invention, the plate is constructed so as to be radio-opaque. This allows the implant to be easily viewed by X-ray after surgery, advantageously allowing progress monitoring. A suture is placed around the drainage tube and knotted to close off the tube and prevent initial flow between the anterior chamber and elastomeric plate. Once bleb tissue formation is complete the suture is removed in a second surgical procedure. Alternatively, a dissolving suture can be used to secure the drainage tube.

In an alternative embodiment, the device includes a dissolving plug contained within the drainage tube. The plug prevents the drainage of aqueous fluid until formation of the bleb is completed. Once bleb formation has occurred, the plug dissolves, allowing for unrestricted flow between the anterior chamber and bleb. Additional alternative embodiments are disclosed wherein the drainage tube comprises double lumen tubing having a primary lumen and a substantially smaller secondary lumen. The primary lumen is provided with a dissolving plug which prevents aqueous flow until bleb formation is complete. The secondary lumen is provided with a flow restrictor or valve to allow initial flow between the anterior chamber and bleb. In a further alternative embodiment, the drainage tube comprises first and second parallel drainage tubes fitted with a dissolving plug and flow restrictor.

BRIEF DESCRIPTION OF THE DRAWINGS

FIG. 3 and FIG. 4 are perspective views illustrating the implant of the present invention;

FIG. 6 shows an additional alternative embodiment of the present invention;

FIG. 7 illustrates a further embodiment of the implant.

DETAILED DESCRIPTION OF THE INVENTION

Figure 1:
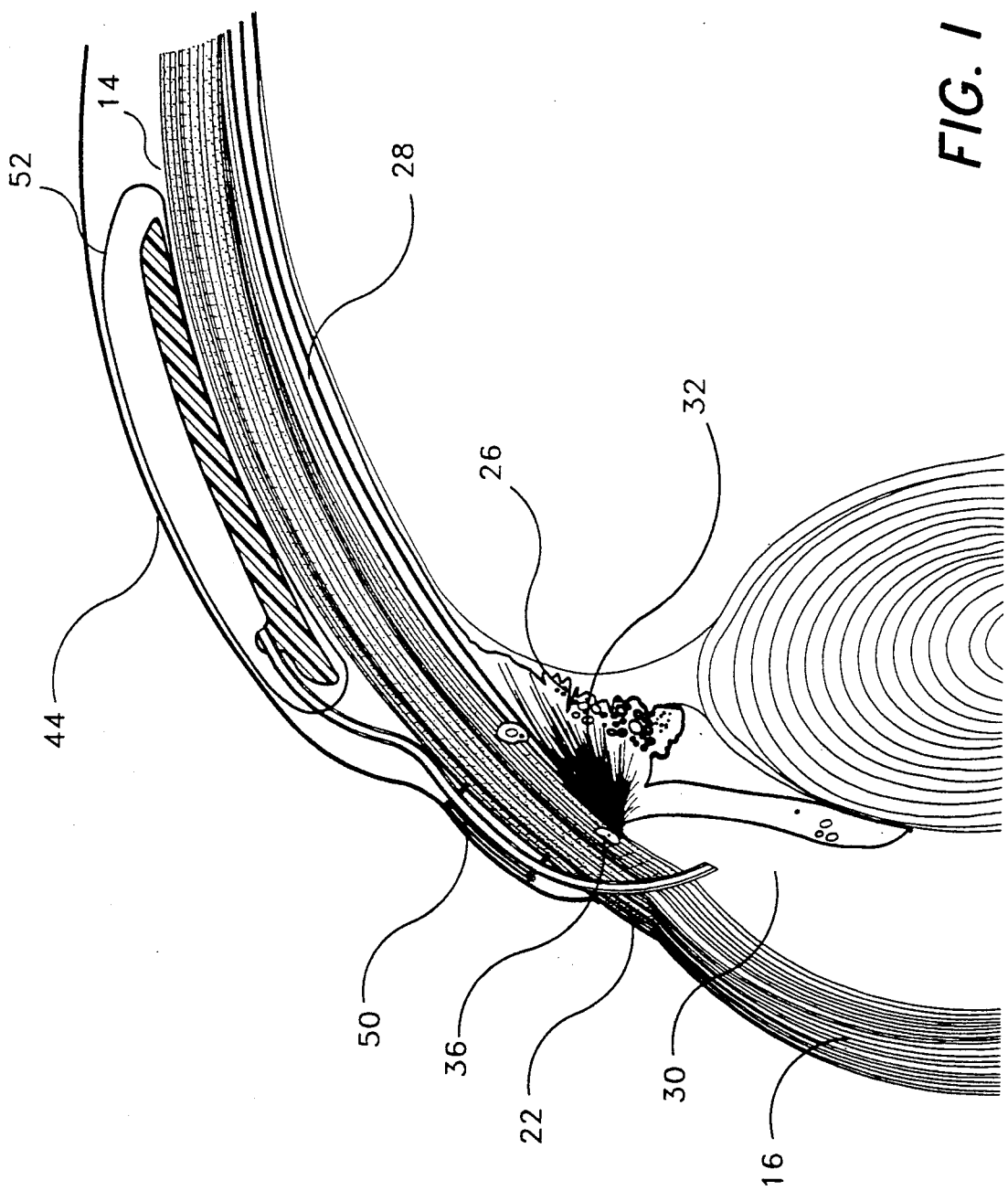
FIG. 1 is a sectional view taken vertically through the upper, frontal portion of the eye.
Figure 2:
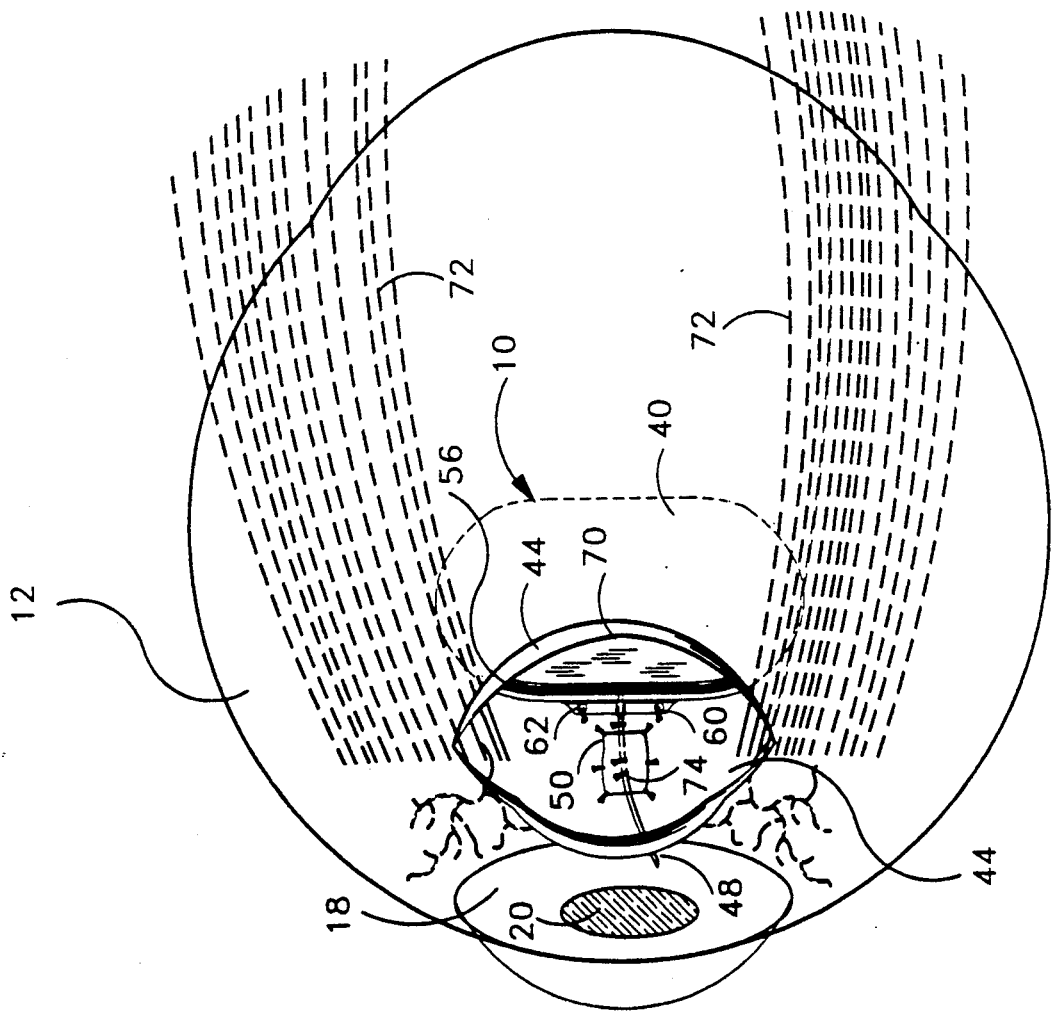
FIG. 2 is a schematic, perspective view of the eye, both illustrating the present invention implanted in a human eye.

FIG. 1 and FIG. 2 illustrate an implant 10 constructed in accordance with the present invention positioned within the tissue of an eye 12. The relevant structure of the eye 12 will be described briefly below so as to provide background for the anatomical terms incorporated herein, however, it should be realized that several anatomical details have been omitted for clarity of understanding. The tough outer membrane known as the sclera 14 covers all of the eye 12 except that portion covered by the cornea 16, the thin, transparent membrane which covers the iris 18 and the pupil 20. The cornea 16 merges into the sclera 14 at a juncture referred to as the limbus 22. The ciliary body 26 begins at the limbus 22 and extends along the interior of the sclera 14 and becomes the choroid 28. The choroid 28 is a vascular membrane which extends along the retina back toward the optic nerve.

It is well-known that aqueous is produced by the ciliary body 26 and reaches the anterior chamber 30 formed between the iris 18 and the cornea 16 through the pupil 20. In a normal eye, the aqueous is removed through the trabecular meshwork 32. There the aqueous passes through Schlemm's canal 36 and through veins which merge with blood-carrying veins and into venous circulation. Intraocular pressure is maintained in the eye 12 by the intricate balance of secretion and absorption or outflow of the aqueous in the manner described above. Glaucoma results from excessive buildup of aqueous fluid in the anterior chamber 30 which produces an increase in intraocular pressure.

The present invention is designed for treatment of glaucoma by facilitating the outflow of the aqueous in the anterior chamber 30 of the eye 12. The implant 10 comprises a pliable carrier plate 40 connected to a drainage tube 42. As illustrated in FIG. 1, the carrier plate 40 is implanted in the eye 12 beneath a layer of Tenon's capsule 44 and sutured to the sclera 14. The discharge tube 42 comprises a first end 46 a second end 48 wherein the first end 46 is attached to the plate 40. The second end 48 of the tube 42 extends through the layer of Tenon's capsule 44 and through the cornea 16 into the anterior chamber 30 of the eye 12. A scleral graft 50 covers the exposed portion of the tube 42 located between the Tenon's capsule 44 and the cornea 16. A large drainage bleb 52 surrounds the carrier plate 40 and lifts the layer of Tenon's capsule 44 above the sclera 14.

The implant 10 is shown in more detail in FIG. 2 and FIG. 3. The carrier plate 40 is generally spherical in shape, and has a perimeter which is elliptical. The surface area of the plate 40 is preferably in the range of 100 to 600 mm$^2$ depending on glaucoma condition and the radius of curvature of the plate is preferably 12 to 14 mm. The carrier plate 40 includes a raised ridge 56 formed adjacent one of the larger-radius perimeter edges of the ellipse, on the convex spherical surface. The rounded edge of the plate 40 extending on either side of the raised ridge 56, not including that portion of the plate 40 adjacent the ridge 56, is entirely radiused, tapered, and blended so as to facilitate insertion as described below. The inner surface of the carrier plate 40 is concave so as to conform to the curvature of the eye 12 and the curvature of the ridge 56 matches the curvature of the sclera 14. An extension 58 of the carrier plate 40 is formed adjacent the ridge 56 and includes two small suture holes 60, 62. The thickness of the plate 40 is preferably in the range of 0.5 to 2.0 mm.

The drainage tube 42 is connected to the carrier plate 40 with adhesive, such as Clear Silicone Rubber Adhesive RTV-118 manufactured by General Electric Silicone Products of Waterford, N.Y., via a small hole 64 formed in the ridge 56 and is bonded to the plate 40 using well-known bonding techniques. The first end of the tube 46 thus drains into the recess formed at the junction of the ridge 56 and the smooth outer surface of the carrier plate 40. The plate 40 is preferably formed of silicone elastomer, such as SILASTIC™, Medical Grade Q7-4765, 65 Shore A, manufactured by Dow Corning Corporation of Midland, Mich., although other silicone elastomers in the range of 40–85 Shore A and having good elastic memory are also suitable. The silicone elastomer is filled with a radiopaque material, such as Barium Sulfate, so that the implant is visible in X-ray procedures, thereby allowing patient progress monitoring. The drainage tube 42 is preferably a 1.0 to 3.0 French flow tube, approximately 10 mm in length, formed of SILASTIC™, Medical Grade RX-50, also available from Dow Corning Corporation.

The present invention can be implanted using known opthalmological surgical techniques and, with reference to FIG. 1 and FIG. 4, the surgical implant procedure will be briefly described. An initial incision 70 is made in the Tenon's capsule 44 proximal the limbus 22. The carrier plate 40 is inserted through this incision 70 and positioned beneath the Tenon's capsule 44 and a portion of the rectus muscle 72, thus covering the sclera 14. The carrier plate 40 can be sutured to the sclera 14, or alternatively, to the rectus muscle 72 if a larger implant 10 is used, with the suture holes 60, 62. The drainage tube 42 is tunneled out through the Tenon's capsule 44 and in through the limbus 22 such that the second end 48 of the tube 42 extends into the anterior chamber 30 of the eye 12. The exposed portion of the drainage tube 42 is then covered with the scleral graft 50. The drainage tube 42 is sutured closed with a suture(s) 74 to prevent any drainage of aqueous prior to formation of the bleb tissue 52 over the carrier plate 40.

The formation of the bleb 52 occurs in response to the introduction of the carrier plate 40 into the tissue of the eye 12. The bleb 52 comprises a thin layer of connective tissue which encapsulates the carrier plate 40, thus lifting the Tenon's capsule 44 above the sclera 14 as shown. Typically, bleb formation occurs in the range of 2 to 8 weeks postoperatively, at which time additional surgery can be performed to remove the suture 74 and allow flow of aqueous from the anterior chamber 30 to the bleb 52 via the drainage tube 42. Alternatively, a dissolving suture can be used to seal the drainage tube 42. After removal or dissolution of the suture 74 blocking the drainage tube 42, the aqueous flow between the tube 42 and bleb 52 is advantageously a patent flow, allowing for both flow from the anterior chamber 30 to the bleb 52 and vice versa. This ensures that retrograde flow from the bleb 52 to the anterior chamber 30, occurring in response to pressure on the eye 12 from the outside, for example, when the lid is forced closed or when the eyeball is pressed on with a finger, does not adversely or harmfully affect intraocular pressure within the eye 12. The fluid contained in the bleb 52 seeps through the bleb into intracellular spaces within eye 12 and is then removed through surrounding capillaries or lymphatics.

The flexible, elastomeric material used to form the present invention and its elliptical shape allow the implant 10 to be inserted much more easily than previously realized with other glaucoma treatment implants. During the insertion process, the carrier plate 40 can be "folded" in half about the axis of the tube 42 and then inserted through the incision 70. Once placed through the incision 70, the carrier plate 40 will return to its original shape and can be positioned so as to cover the sclera 14, as described above. Further, the material from which the plate 40 is formed is soft and pliable, which results in much less trauma and irritation to the surrounding tissues and vasculature than experienced with a rigid plate device. In addition, since the plate 40 is folded, a smaller incision can be made in the Tenon's capsule 44. Thus, the pliable carrier plate 40 significantly decreases the surgical procedure length while also minimizing tissue and vasculature damage which can occur in the insertion process.

Figure 5:
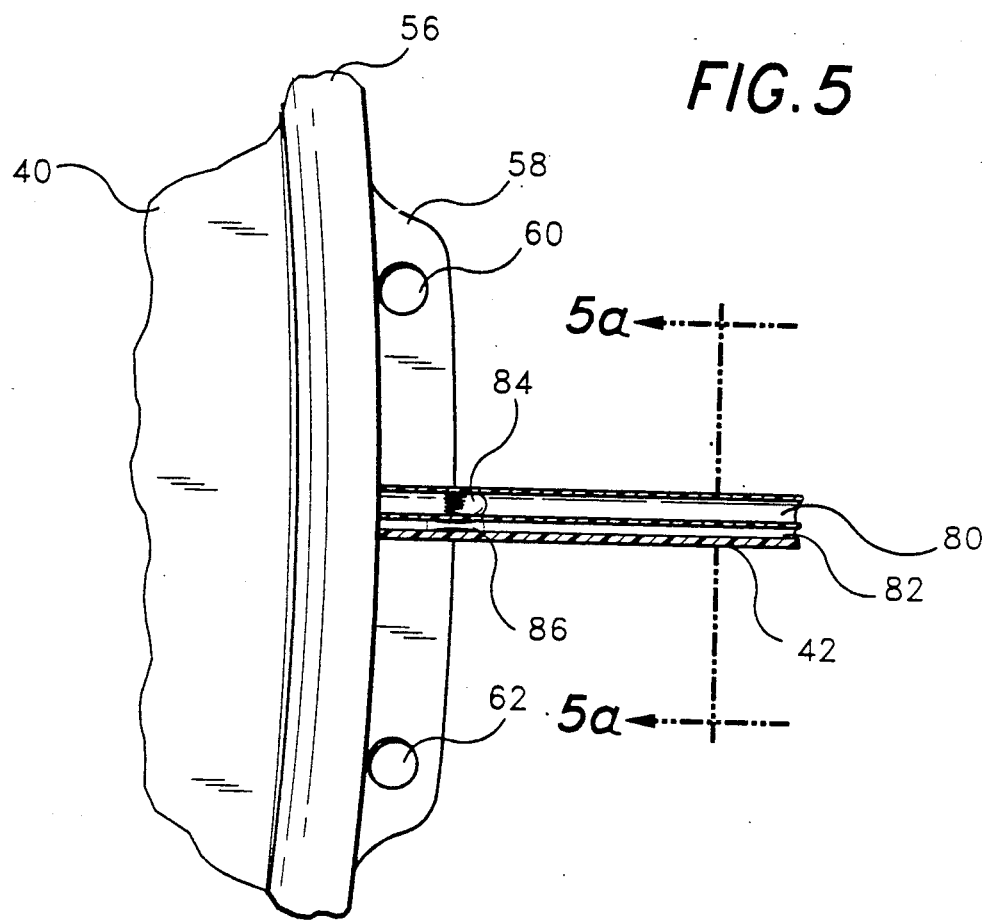
FIG. 5 is an alternative embodiment of the drainage tube.
Figure 5A:
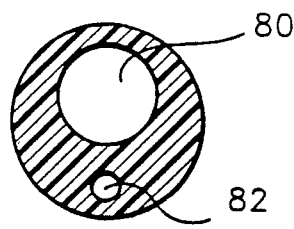
FIGS. 5a through 5d are cross-sectional views illustrating various configurations of the drainage tube of FIG. 5.
Figure 5B:
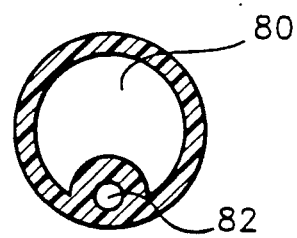
Figure 5C:
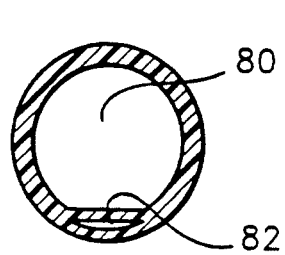
Figure 5D:
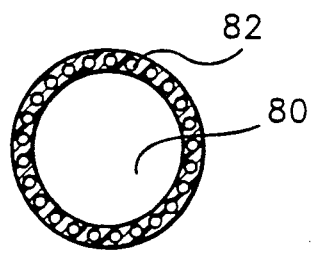

In an alternative embodiment illustrated in FIG. 5, the drainage tube 42 is formed as double lumen tubing having a primary lumen 80 and a secondary lumen 82 substantially smaller than the primary lumen 80. A dissolving plug 84 is placed within the primary lumen 80 to ensure that the majority of aqueous flow does not begin until formation of the bleb 52 is complete. The secondary lumen 82 is provided with a flow restrictor, small valve, or filter 86 which allows for a small amount of initial aqueous flow during bleb formation. The dissolving plug 84 is preferably formed of Poly Vinyl Alcohol (PVA), Poly Vinyl Pyrolidone (PVP), enzymatically activated collagen, or other biomedically suitable materials which slowly dissolve, thus gradually permitting the flow of aqueous and relieving intraocular pressure. As shown in FIGS. 5a through 5d, a variety of primary and secondary lumen 80, 82 configurations are possible. Although four configurations are illustrated, one skilled in the art will recognize that various other embodiments could be constructed.

Another alternative embodiment of the present invention is illustrated in FIG. 6. FIG. 6 illustrates an implant 88 having a carrier plate 40, a raised ridge 56, a plate extension 58, and suture holes 60, 62, essentially identical to that disclosed and shown in FIGS. 2 and 3 and numbered correspondingly. The implant 88 is attached to the eye 12 in the same manner as shown in FIGS. 1 and 4 so as to provide aqueous flow between the anterior chamber 30 and bleb 52. The implant 88 includes first and second parallel drainage tubes 90, 92 positioned adjacent the suture holes 60, 62 and bonded to the raised ridge 56. The first discharge tube 60 is fitted with a dissolving plug 94 which slowly dissolves to provide gradual flow from the anterior chamber 30 to the bleb 52. As described above, the plug 94 is formed of a polymeric material such as PVP, PVA, or collagen. Alternatively, a ligature could be used to secure the first tube 90 and control flow between the anterior chamber 30 and bleb 52. A micron filter or flow restrictor 96 is contained within the second discharge tube 62 to provide a relatively small amount of initial flow between the anterior chamber 30 and bleb 52.

A further alternative embodiment of the invention is illustrated in FIG. 7 wherein first and second discharge tubes 100, 102, are oriented in a "Y" configuration and merge into a single discharge tube 104 whose end 106 is placed inside the anterior chamber 30. As in the embodiment described above and illustrated in FIG. 6, the first discharge tube 100 includes a dissolving plug 94 and the second discharge tube includes a flow restrictor or valve 96 placed therein. In this manner, aqueous flow is controlled until formation of the bleb 52 is complete.

Although the invention has been described with reference to specific embodiments, the description is intended to be illustrative of the invention and is not intended to be limiting. Various modifications and applications may occur to those skilled in the art without departing from the true spirit and scope of the invention as defined in the appended claims.

What is claimed is:

1. An implant for draining aqueous fluid from an eye, comprising:
    a thin, elastomeric plate having first and second surfaces joined at the plate perimeter, said perimeter of said plate being elliptical, said first and second surfaces curved spherically to conform to the curvature of said eye; and
    an elastomeric drainage tube attached to said plate, said drainage tube comprising a first end and a second end, said first end open onto one of said first and second surfaces of said elastomeric plate and wherein said second end extends for connection with said eye to provide fluid communication between said eye and said one of said first and second surfaces of said elastomeric plate, wherein said drainage tube includes a dissolving plug positioned therein, said dissolving plug for controlling said flow between said eye and one of said first and second surfaces of said elastomeric plate.

2. An implant for draining aqueous fluid from an eye, comprising:
- a thin, elastomeric plate having first and second surfaces joined at the plate perimeter, said perimeter of said plate being elliptical, said first and second surfaces curved spherically to conform to the curvature of said eye; and
- an elastomeric drainage tube attached to said plate, said drainage tube comprising a first end and a second end, said first end open onto one of said first and second surfaces of said elastomeric plate and wherein said second end extends for connection with said eye to provide fluid communication between said eye and said one of said first and second surfaces of said elastomeric plate, wherein said drainage tube includes a dissolving plug positioned therein, said dissolving plug for controlling said flow between said eye and one of said first and second surfaces of said elastomeric plate, wherein said drainage tube further comprises a secondary lumen having diameter smaller than the diameter of said discharge tube, said secondary lumen for providing initial flow between said eye and one of said first and second surfaces of said elastomeric plate.

3. An implant for draining aqueous fluid from an eye, comprising:
- a thin, elastomeric plate having first and second surfaces joined at the plate perimeter, said perimeter of said plate being elliptical, said first and second surfaces curved spherically to conform to the curvature of said eye; and
- an elastomeric drainage tube attached to said plate, said drainage tube comprising a first end and a second end, said first end open onto one of said first and second surfaces of said elastomeric plate and wherein said second end extends for connection with said eye to provide fluid communication between said eye and said one of said first and second surfaces of said elastomeric plate, wherein said drainage tube comprises first and second drainage tubes, said first drainage tube having a dissolving plug positioned therein, said second drainage tube having a flow restrictor positioned therein, wherein said dissolving plug and said flow restrictor control aqueous flow between one of said first and second surfaces of said elastomeric plate and said eye.

4. An implant for draining aqueous fluid from an eye, comprising:
- a thin, elastomeric plate having first and second surfaces joined at the plate perimeter, said perimeter of said plate being elliptical, said first and second surfaces curved spherically to conform to the curvature of said eye; and
- an elastomeric drainage tube attached to said plate, said drainage tube comprising a first end and a second end, said first end open onto one of said first and second surfaces of said elastomeric plate and wherein said second end extends for connection with said eye to provide fluid communication between said eye and said one of said first and second surfaces of said elastomeric plate, wherein said drainage tube comprises first and second drainage tubes, said first drainage tube having a dissolving plug positioned therein, said second drainage tube having a flow restrictor positioned therein, wherein said dissolving plug and said flow restrictor control aqueous flow between one of said first and second surfaces of said elastomeric plate and said eye, wherein said dissolving plug is formed of PVA, PVP, or collagen.

5. An implant for draining aqueous fluid from an eye, comprising:
- a thin, elastomeric plate having first and second surfaces joined at the plate perimeter, said perimeter of said plate being elliptical, said first and second surfaces curved spherically to conform to the curvature of said eye; and
- an elastomeric drainage tube attached to said plate, said drainage tube comprising a first end and a second end, said first end open onto one of said first and second surfaces of said elastomeric plate and wherein said second end extends for connection with said eye to provide fluid communication between said eye and said one of said first and second surfaces of said elastomeric plate, wherein said drainage tube comprises first and second drainage tubes, said first drainage tube secured with a ligature, said second drainage tube having a flow restrictor positioned therein, wherein said ligature and said flow restrictor control aqueous flow between one of said first and second surfaces of said elastomeric plate and said eye to control flow between one of said first and second surfaces of said elastomeric plate and said eye.

6. A method of inserting an implant into an eye for treatment of glaucoma, said implant comprising an elastomeric plate attached to an elastomeric drainage tube, comprising the steps of:
- making an incision in the Tenon's capsule of said eye;
- folding said elastomeric plate to reduce its size;
- inserting said folded elastomeric plate into said incision;
- releasing said folded elastomeric plate such that said plate returns to its original configuration;
- positioning said plate over the sclera of said eye beneath said Tenon's capsule; and
- positioning said drainage tube within said eye so as to provide fluid communication between said eye and said elastomeric plate.

7. The method of claim 6, further comprising the step of suturing said elastomeric plate to the sclera of said eye to secure said implant to said eye.

8. The method of claim 6, wherein the step of positioning said drainage tube within said eye comprises placing said drainage tube in said anterior chamber of said eye.

9. The method of claim 6, further comprising the step of ligating said drainage tube so as to prevent initial aqueous flow through said drainage tube.

* * * * *